United States Patent
De Vries et al.

(10) Patent No.: US 9,411,064 B2
(45) Date of Patent: Aug. 9, 2016

(54) TESTERS FOR ACOUSTIC SENSORS

(75) Inventors: Thomas De Vries, Manama (BH); Gary D. Althoff, Houston, TX (US); Eugene LaCarmie, Lafayette, LA (US)

(73) Assignee: Halliburton Energy Services, Inc., Houston, TX (US)

( * ) Notice: Subject to any disclaimer, the term of this patent is extended or adjusted under 35 U.S.C. 154(b) by 237 days.

(21) Appl. No.: 14/008,409

(22) PCT Filed: Jul. 26, 2011

(86) PCT No.: PCT/US2011/045365
§ 371 (c)(1),
(2), (4) Date: Sep. 27, 2013

(87) PCT Pub. No.: WO2013/015790
PCT Pub. Date: Jan. 31, 2013

(65) Prior Publication Data
US 2014/0137633 A1    May 22, 2014

(51) Int. Cl.
*G01N 29/30* (2006.01)
*G01V 1/40* (2006.01)
*G01N 13/00* (2006.01)

(52) U.S. Cl.
CPC *G01V 1/40* (2013.01); *G01N 13/00* (2013.01); *G01N 29/30* (2013.01)

(58) Field of Classification Search
CPC ..... G01N 29/30; G01N 29/024; G01H 3/005; G01V 13/00; G01V 1/40
USPC .......................................................... 73/1.82
See application file for complete search history.

(56) References Cited

U.S. PATENT DOCUMENTS

| 4,106,327 A * | 8/1978 | Adler ...................... G01H 5/00 73/1.83 |
| 4,226,162 A | 10/1980 | Ebach |
| 5,437,178 A * | 8/1995 | Esin ...................... G01F 23/296 367/7 |
| 5,837,880 A | 11/1998 | Shakinovsky et al. |
| 2010/0126275 A1 | 5/2010 | Leyh et al. |

FOREIGN PATENT DOCUMENTS

| DE | 3807383 A1 * | 9/1989 | .......... G06S 7/52004 |
| GB | 166512 A | 4/1921 | |
| GB | 533508 A | 8/1939 | |
| WO | WO-2007097727 A1 | 8/2007 | |
| WO | WO-2013015790 A1 | 1/2013 | |

OTHER PUBLICATIONS

"International Application Serial No. PCT/US2011/045365, International Preliminary Report on Patentability mailed Nov. 14, 2013", 16 pgs.
"International Application Serial No. PCT/US2011/045365, International Search Report mailed Apr. 2, 2012", 4 pgs.
"International Application Serial No. PCT/US2011/045365, Written Opinion mailed Apr. 2, 2012", 7 pgs.

* cited by examiner

*Primary Examiner* — Hezron E Williams
*Assistant Examiner* — Nashmiya Fayyaz
(74) *Attorney, Agent, or Firm* — Schwegman, Lundberg & Woessner, P.A.; Alan Bryson (57) ABSTRACT

Various embodiments include apparatus and methods to test an acoustic sensor. Apparatus and methods can include collecting an acoustic wave from a transmitter of the acoustic sensor and directing the acoustic wave to a receiver of the acoustic sensor along a path different from the acoustic sensor. Additional apparatus, systems, and methods are disclosed.

31 Claims, 7 Drawing Sheets

TESTERS FOR ACOUSTIC SENSORS

RELATED APPLICATIONS

This application is a U.S. National Stage Filing under 35 U.S.C. 371 from International Application No. PCT/US2011/045365, filed on 26 Jul. 2011, and published as WO 2013/015790 A1 on 31 Jan. 2013, which application and publication are incorporated herein by reference in their entirety.

TECHNICAL FIELD

The present invention relates generally to apparatus for making measurements related to oil and gas exploration.

BACKGROUND

In drilling wells for oil and gas exploration, understanding the structure and properties of the associated geological formation provides information to aid such exploration. Measurements in a borehole are typically performed using a variety of tools to attain this understanding. Measurement tools can include acoustic sensors. The usefulness of measurements made using acoustic sensors may be related to the precision or quality of the information derived from such measurements, which in turn depends on the components of these tools functioning properly.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, apparatus and methods are provided to test an acoustic sensor. Such apparatus and methods of using the apparatus can provide a mechanism to determine whether receivers on an acoustic sensor tool are functioning properly. In addition, the health of transmitters and receivers on an acoustic sensor tool can be determined. Apparatus and methods can include collecting an acoustic wave from a transmitter of the acoustic sensor and directing the acoustic wave to a receiver of the acoustic sensor along a path isolated from the acoustic sensor. Components can be arranged to allow acoustic waves to travel to the receivers of the acoustic sensor consistently, allowing consistent testing results of a variety of acoustic sensor tools. Such sensor tools can include, but are not limited to, a bi-modal acoustic sensor.

Figure 1:
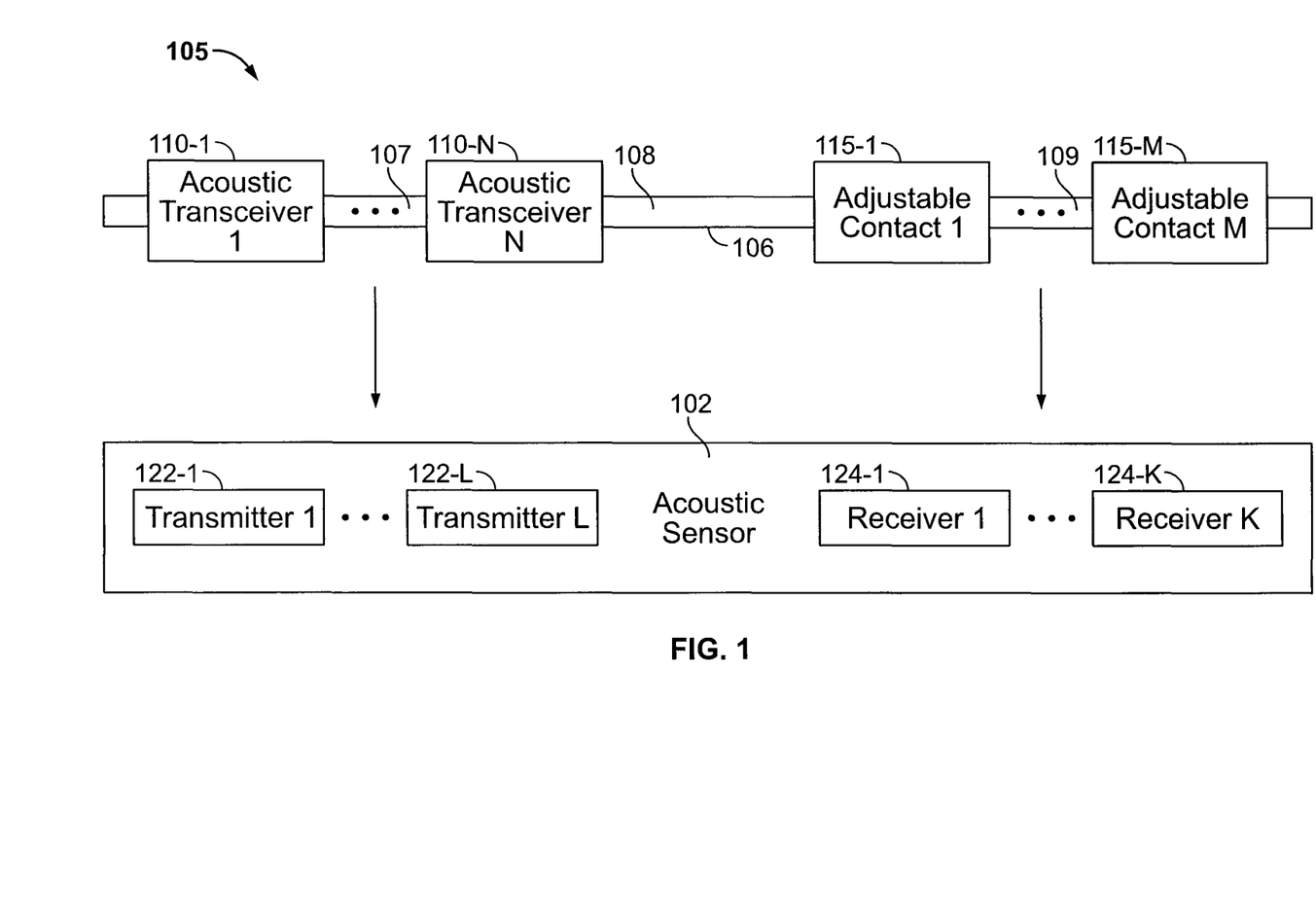
FIG. 1 shows a block diagram of an example tester arranged to test an acoustic sensor, in accordance with various embodiments.

FIG. 1 shows an example embodiment of a tester 105 of an acoustic sensor 102. Tester 105 includes acoustic transceivers 110-1 . . . 110-N and adjustable contacts 115-1 . . . 115-M coupled by a sound conducting member 106 having a first end region 107, a second end region 109, and a sound conducting portion 108 between the first end region 107 and the second end region 109. An acoustic transceiver herein means a device that receives an acoustic wave and transmits the acoustic wave. The transmitted acoustic wave may be modified in the acoustic transceiver. For example, an acoustic transceiver can be structured to collect an acoustic wave, amplify the acoustic wave, and transmit the amplified acoustic wave. An acoustic transceiver can be structured to transmit an acoustic wave by redirecting a received acoustic wave along a path different from the path on which the acoustic wave is received. An acoustic transceiver can be structured to transmit an acoustic wave by focusing a received acoustic wave. The various forms of an acoustic transceiver can incorporate mechanical components such as membranes and other sound related structures. An acoustic transceiver can include a device that receives an acoustic wave, converts the acoustic wave to another format such as an electrical signal, operates on the other format, converts the other format to an acoustic wave, and transmits the converted acoustic wave. Selection of the structure of an acoustic transceiver of tester 105 can depend upon the application of tester 105. In various embodiments, one or more of acoustic transceivers 110-1 . . . 110-N are realized as a head of stethoscope, which can be referred to as a stethoscope head.

An acoustic wave collected by one or more of acoustic transceivers 110-1 . . . 110-N, coupled to first region 107, can be transmitted to adjustable contacts 115-1 . . . 115-M, coupled to first region 109, by sound conducting portion 108. A sound conducting member is a structure that readily conducts an acoustic wave. Sound conducting member 106 can be structured having a number of different shapes. Sound conducting member 106 can be structured as, but not limited to, a flat piece of metal, a metal rod, or combinations of a flat piece of metal and a metal rod. For example, sound conducting member 106 can have a metal rod as sound conducting portion 108 and a flat piece of metal, such as an acoustic bar, as second end 109. The flat piece of metal can be a flat piece of steel. The metal rod can be a steel rod. Other materials or combinations of materials can be used in the construction of sound conducting member 106 based on the capacity of such materials or combinations of materials to conduct an acoustic wave for a distance along a specified path such that the acoustic wave can be detected at the end of the path.

Tester 105 can be arranged to test acoustic sensor 102 with one or more adjustable contacts 115-1 . . . 115-M arranged to selectively contact one or more receivers 124-1 . . . 124-K of acoustic sensor 102 when one or more of acoustic transceivers 110-1 . . . 110-N are positioned on one or more of transmitters 122-1 . . . 122-L of acoustic sensor 102. Each of adjustable contacts 115-1 . . . 115-M can be arranged to contact at most one of receivers 124-1 . . . 124-K. Adjustable contacts 115-1 . . . 115-M can be structured such that an acoustic wave received from acoustic transceivers 110-1 . . . 110-N is directed to one or more receivers 124-1 . . . 124-K. When the number of receivers is less than the number of adjustable contacts (K<M), adjustable contacts, M–K in number, can be adjusted such that these adjustable contacts do not couple to acoustic sensor 102 with the remaining adjustable contacts connected to acoustic sensor 102. With K>M, testing of acoustic sensor may be facilitated by making a number of measurements with tester 105 arranged in multiple orientations with respect to acoustic sensor 105. This may be accomplished with sound conducting member 106 adjustable to different lengths. Different lengths can be realized with sound conducting member 106 having connectable sections that maintain sound conduction when adjusted to different lengths.

Testing of acoustic sensor 102 can be conducted with acoustic sensor 102 having a single transmitter 122-1 generating an acoustic wave received at each of receivers 124-1 . . . 124-K via respective adjustable contacts 115-1 . . . 115-M. Adjustable contacts 115-1 . . . 115-M can be adjusted such that an acoustic wave generated from one of transmitters 122-1 . . . 122-L is received by a selected number of receivers 124-1 . . . 124-K. Various test probes can be generated at different frequencies in the testing of acoustic sensor 102.

A tester of an acoustic sensor can be realized in a variety of configurations. Tester 105 can be structured as a single tester as shown in FIG. 1. With acoustic sensor 102 having transmitters and receivers on different sides of the body of acoustic sensor 102, tester 105 can be attached to acoustic sensor 102 multiple times, tested in each attachment, to account for the arrangement of transmitters and receivers on different sides of the body of acoustic sensor 102. Alternatively, a test can be structured as multiple testers 105, each attached respective sides of acoustic sensor 102. Further, a tester is not limited to the linear example shown in the block diagram of FIG. 1. With receivers of an acoustic sensor arranged in a pattern other than a linear pattern, adjustable contacts 115-1 . . . 115-M can be arranged on end 109 in a pattern correlated to the pattern of receivers 124-1 . . . 124-K in acoustic sensor 102.

Tester 105 can include components to aid in directing an acoustic wave from adjustable contacts 115-1 . . . 115-M to respective receivers 124-1 . . . 124-K in acoustic sensor 102 when coupled to acoustic sensor. Tester 105 can include a material covering sound conducting portion 106, where the material is selected to isolate substantially the acoustic wave within or along the sound conducting portion 108. The selected material can include, but is not limited to, a rubber hose. Tester 105 can be constructed with components to operatively channel the acoustic wave to receivers 124-1 . . . 124-K, where the components are structured to align adjustable contacts 115-1 . . . 115-M to the respective receivers 124-1 . . . 124-K. These components can be realized by a suction cups through which adjustable contacts 115-1 . . . 115-M extend from the sound conducting member 106. Adjustable contacts 115-1 . . . 115-M can be constructed with features to adjust their contact to receivers 124-1 . . . 124-K. Each of adjustable contacts 115-1 . . . 115-M can include a swivel portion at an end of the adjustable contact to contact a respective receiver of receivers 124-1 . . . 124-K. The swivel portion furnishes a mechanism operable to provide correction to an alignment error when coupling tester 105 to acoustic sensor 102. An additional aid to couple tester 105 to acoustic sensor 102 can include hook and loop straps such as Velcro® straps. Velcro® straps attached to tester 105 may be used to ensure a good solid fitment of tester 105 onto acoustic sensor 102 being tested.

As noted, adjustable contacts 115-1 . . . 115-M can be constructed to selectively engage respective receivers of acoustic sensor 102. The selective engagement by adjustable contacts 115-1 . . . 115-M can be attained by the manner in which adjustable contacts 115-1 . . . 115-M are constructed in tester 105. Adjustable contacts 115-1 . . . 115-M can be positioned through respective regions on end 109 of sound conducting member 106 such that these regions allow the selective motion of adjustable contacts 115-1 . . . 115-M and these regions conduct an acoustic wave from sound conduction portion 108 to its respective adjustable contacts 115-1 . . . 115-M. These regions can be metal regions. These regions can be provided by second end region 109 or as a region attached to second end region 109. To isolate the propagation of an acoustic wave, adjustable contacts 115-1 . . . 115-M to respective receivers 124-1 . . . 124-K during testing of acoustic sensor 102, an insulating material can be arranged to contact acoustic sensor 102 such that the insulating material separates the metal region from acoustic sensor 102 when tester 105 is coupled to acoustic sensor 102. Each of adjustable contacts 115-1 . . . 115-M can be constructed through its respective metal region and through the insulating material.

Adjustable contacts 115-1 . . . 115-M can be provided in a number of constructions that conduct an acoustic wave. For example, adjustable contacts 115-1 . . . 115-M can be arranged as bolts that engage a nut, where the nut affixed to the metal region that couples an acoustic wave from sound conducting portion 108. Adjustment of bolts 115-1 . . . 115-M can be provided by movement of bolts 115-1 . . . 115-M via their respective nuts. The nuts can be affixed to their respective metal regions by welding the nuts to their respective metal regions. Adjustable contacts 115-1 . . . 115-M can be realized by other mechanisms. For example, a spring and pin combination can be used with the pin contacting second end region 109 and the spring contacting a receiver of acoustic sensor 102 with tester 105 coupled to acoustic sensor 102. The coupling can be achieved with sufficient pressure to press the spring to the receiver.

Figure 2:
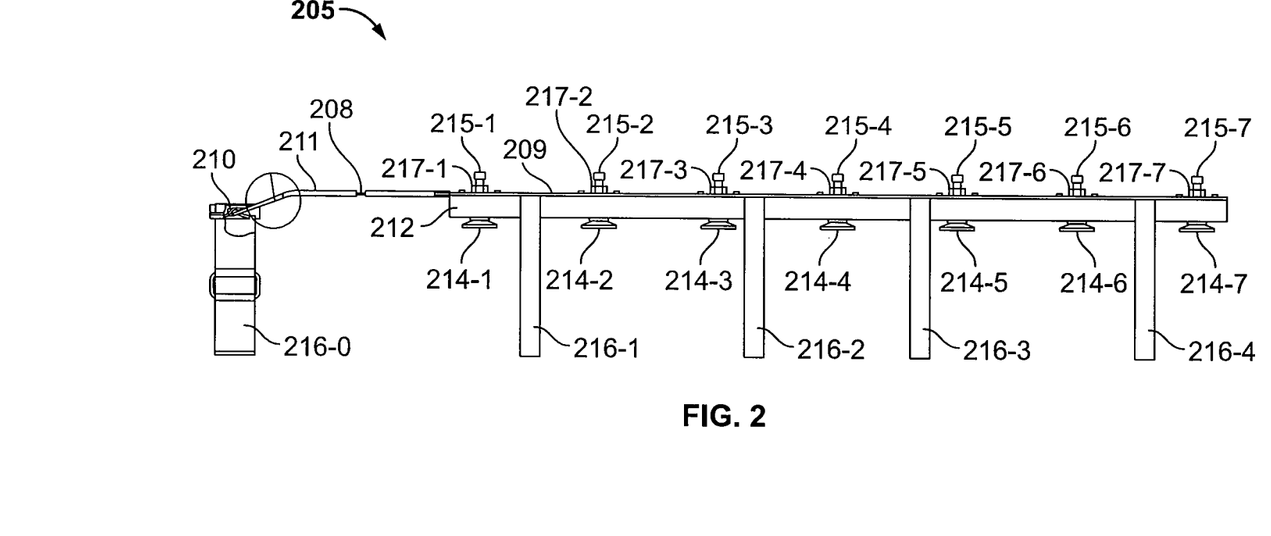
FIG. 2 shows a block diagram of an example tester operable to test an acoustic sensor, in accordance with various embodiments.

FIG. 2 shows an example embodiment of a tester 205 operable to test an acoustic sensor. Tester 205 can be used to verify the proper operation of transmitters and receivers to the acoustic sensor and can be referred to as a verifier. Tester 205 includes a stethoscope head 210, a metal rod 208, suction cups 214-1 . . . 214-7, adjustable length screws 215-1 . . . 215-7, a flat piece of metal 209, an insulating medium 212, an isolating material 211, and hook and loop straps 216-0, 216-1 . . . 216-4. Stethoscope head 210 functions as an acoustic transceiver for tester 205 to transmit an acoustic wave to adjustable length screws 215-1 . . . 215-7, which function as adjustable contacts to deliver the acoustic wave to receivers of the acoustic sensor being tested.

The acoustic wave travels from stethoscope head 210 to the body of verifier 205 by metal rod 208. Metal rod 208 can include, but is not limited to, a stainless steel rod, which may be structured as a thin rod. Metal rod 208 can be covered by isolating material 211. Isolating material 211 can cover metal rod 208 to help isolate the sound wave collected by stethoscope head 210 and transmitted from stethoscope head 210 within the length of metal rod 208 to flat piece of metal 209 connected to metal rod 208. Ideally, isolating material 211 functions as an isolator. Higher amplitude readings can be established using isolating material 211 than without using isolating material 211. Isolating material 211 can include, but is not limited to, a rubber hose.

Stethoscope head 210 can be designed such that, when verifier 205 is positioned to test an acoustic sensor, stethoscope head 210 is positioned to sit directly on top of the transmitter of the acoustic sensor, allowing an acoustic wave from the transmitter to be amplified and sent down metal rod 208 towards flat piece of metal 209 of the body of verifier 205 with maximum amplitude. Metal rod 208 can have a large length such that verifier 205 can be used on an acoustic sensor having transmitter and receivers separated by such lengths.

Metal rod 208 can be inserted into stethoscope head 210 and stethoscope head 210 can be positioned to sit on the face of the transmitter of the acoustic sensor. Metal rod 208 can run from stethoscope head 210 across verifier 205 towards the receiver array of the acoustic sensor. Metal rod 208 makes contact with a piece of metal that sits on top of insulating medium 212. The piece of metal, which can be a steel piece, can be realized as flat piece of metal 209 or as a piece of metal in addition to flat piece of metal 209. Insulating medium 212 can be arranged such that it is placed above and across the entire array of receivers of the acoustic sensor being tested.

Nuts 217-1 . . . 217-7 can be welded to the piece of metal 209, where each nut can be arranged such that it is placed directly above a respective receiver of the acoustic sensor being tested. Holes can be drilled in insulating medium 211 so that each of adjustable length screws (bolts) 215-1 . . . 215-7 can be placed through their corresponding holes. Each of adjustable length screws 215-1 . . . 215-7 can be realized, but is not limited to, as a thrust screw. The thrust screw assembly allows straight line static load thrust without transmitting torsional or radial force on to the contact area of the receivers of the acoustic sensor to which verifier 205 is being applied. The free floating ball design of the thrust screw assembly allows the thrust screw to continue to rotate where the ball remains stationary against the contact surface, while applying a specific torque across the array of receivers. As a result, adjusting the thrust screw effectively does not damage the surface of the receivers in the process.

With nuts 217-1 . . . 217-7 contacting flat piece of metal 209, each of nuts 217-1 . . . 217-7 can transmit the acoustic wave from flat piece of metal 209 through to the adjustable length screws 215-1 . . . 215-7, which in turn makes contact with the receiver face of their associated receiver. Adjustable length screws 215-1 . . . 215-7 can include a swivel feature on the end of each of adjustable length screws 215-1 . . . 215-7. The swivel portion of each screw allows for the correction of a possible alignment error when placing verifier 205 on the acoustic sensor being tested. The swivel feature can be structured such that a base in the assembly can pivot to a certain degree in order to accommodate the angle of the surface of the receiver to secure the screw to the receiver. Nuts 217-1 . . . 217-7 can adjust the pressure that the swivel head of each of adjustable length screws 215-1 . . . 215-7 makes on the surface of its corresponding receiver by applying a larger toque on the head of the screw.

Adjustable length screws 215-1 . . . 215-7 can accommodate an acoustic sensor having an arrangement of 7 receivers and can also accommodate an acoustic sensor having an arrangement of 6 or less receivers. Application to an acoustic sensor having an arrangement of 6 or less receivers can be achieved by backing out one or more of the adjustable length screws 215-1 . . . 215-7 from the acoustic sensor being tested. Adjustable length screws 215-1 . . . 215-7 also provide the capability to adjust the pressure that its swivel portion makes on the surface of the receiver faces through different ranges of torque.

Suction cups 214-1 . . . 214-7 can be structured by drilling a hole through the center of each suction cup such that one of adjustable length screws 215-1 . . . 215-7 can be placed through the hole. Suction cups 214-1 . . . 214-7 can be arranged to sit directly on top of the receivers of the acoustic sensor to be tested. Suction cups 214-1 . . . 214-7 can be used to help channel the acoustic wave within the face of the corresponding receivers of the acoustic sensor. Suction cups 214-1 . . . 214-7 can be used to help align verifier 205 to ensure consistent placement.

Hook and loop straps 216-0, 216-1 . . . 216-4 such as Velcro® straps, which can include industrial Velcro® straps. Hook and loop strap 216-0 can be used in coupling stethoscope head 210 to the acoustic sensor to be tested. Hook and loop straps 216-1 . . . 216-4 can couple the body of verifier 205 to the acoustic sensor to be tested. Hook and loop straps 216-0, 216-1 . . . 216-4 can be used to ensure a good solid fitment of verifier 205 onto the acoustic sensor being tested.

In operation of verifier 205, the transmitter of an acoustic sensor fires an acoustic wave, which is amplified by stethoscope head 210. The transmitter can generate the acoustic wave at a specified frequency. The acoustic wave travels down metal rod 208 towards the receivers of the acoustic sensor. Metal rod 208 comes into contact with flat piece of metal 209, which may be an acoustic bar, placed above insulating medium 211 transferring the sound to each one of the seven nuts 217-1 . . . 217-7. Nuts 217-1 . . . 217-7 make contact with adjustable length screws 215-1 . . . 215-7 towards its swivel head and directly to the face of the receivers of the acoustic sensor being test. Each receiver contacting one to adjustable length screws 215-1 . . . 215-7 picks up the sound wave and records this sound wave in a memory associated with the acoustic sensor. The transmitter can be activated a number of times and the corresponding transmitted waves received in the receivers of the acoustic sensor can also be recorded. In addition, the testing can include generating a plurality of acoustic waves, each having a frequency different from the other acoustic waves. Once generation and collection of probe signals in the memory is completed, the memory associated with the acoustic sensor can be read and the data analyzed. The analysis can include the determination of consistency in the readings and evaluation of specific amplitudes relative to a set threshold. The threshold for amplitudes can be determined based on an established pass or fail criteria for the receivers. This procedure allows for a true acoustic measurement on all receivers of the acoustic sensor.

Figure 3:
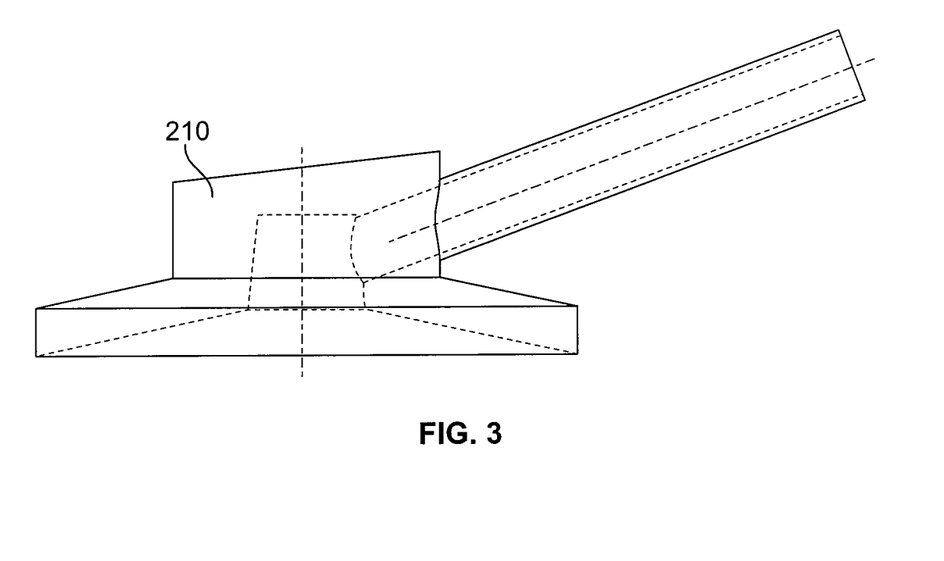
FIG. 3 shows an example of a stethoscope head that can be used in the tester of FIG. 2, in accordance with various embodiments.
Figure 4:
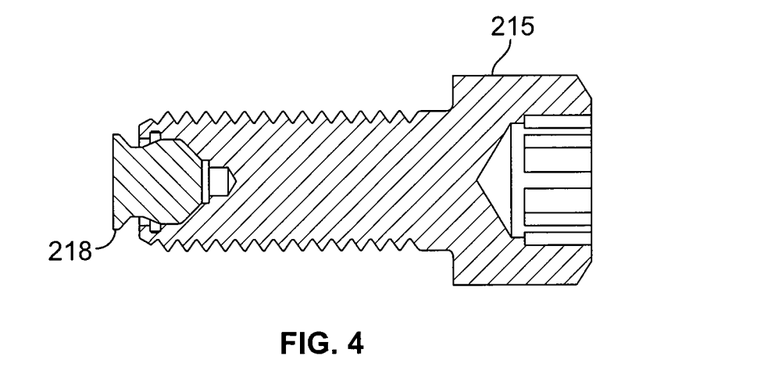
FIG. 4 shows an example of an adjustable length screw that can be used in the tester of FIG. 2, in accordance with various embodiments.
Figure 5:
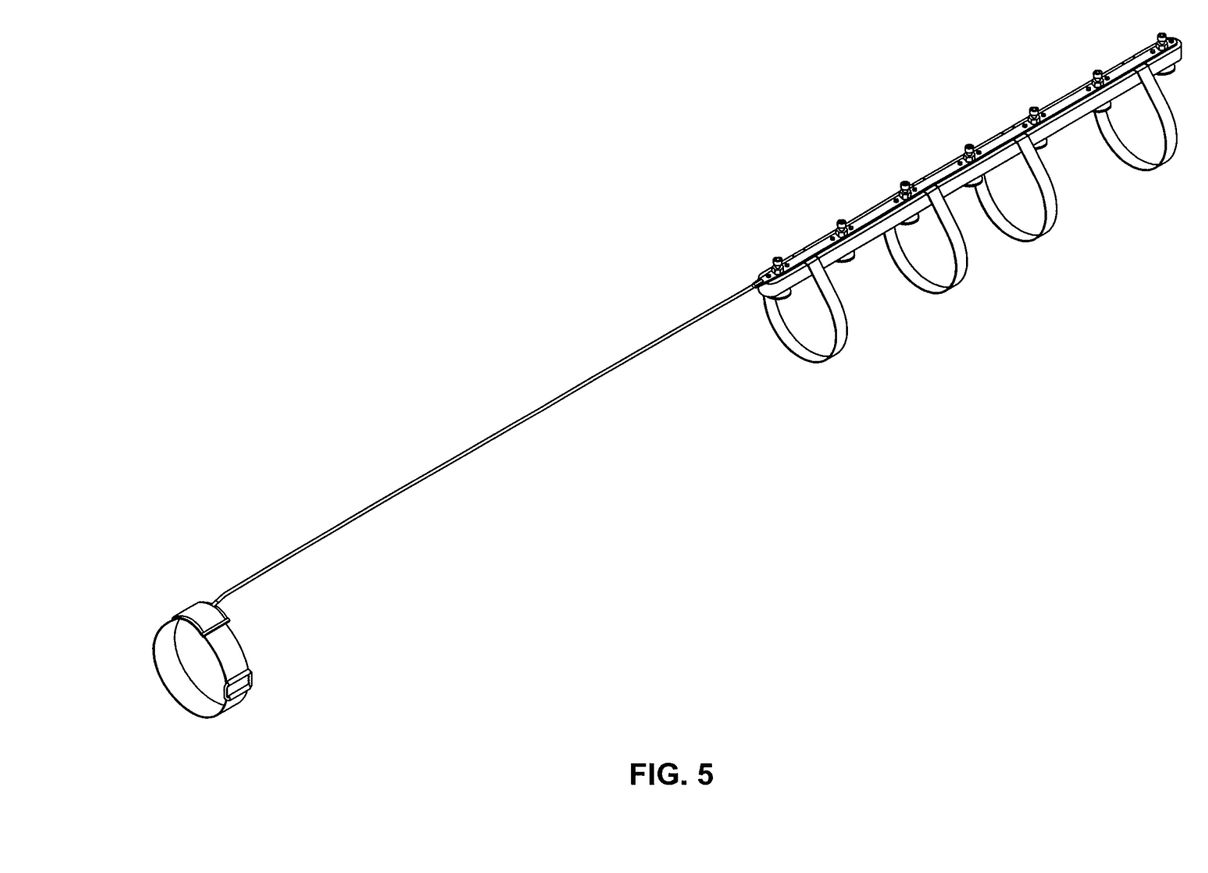
FIG. 5 shows a view of the tester of FIG. 2 illustrating a relatively large distance from the stethoscope head to the body of the tester of FIG. 2, in accordance with various embodiments.

FIG. 3 shows an example embodiment of stethoscope head 210 that can be used in tester 205 of FIG. 2. FIG. 4 shows an example embodiment of an adjustable length screw 215 having a swivel portion 218 that can be used in tester 205 of FIG. 2. FIG. 5 shows a view of the tester of FIG. 2 illustrating a relatively large distance from the stethoscope head to the body of the tester of FIG. 2.

Figure 6:
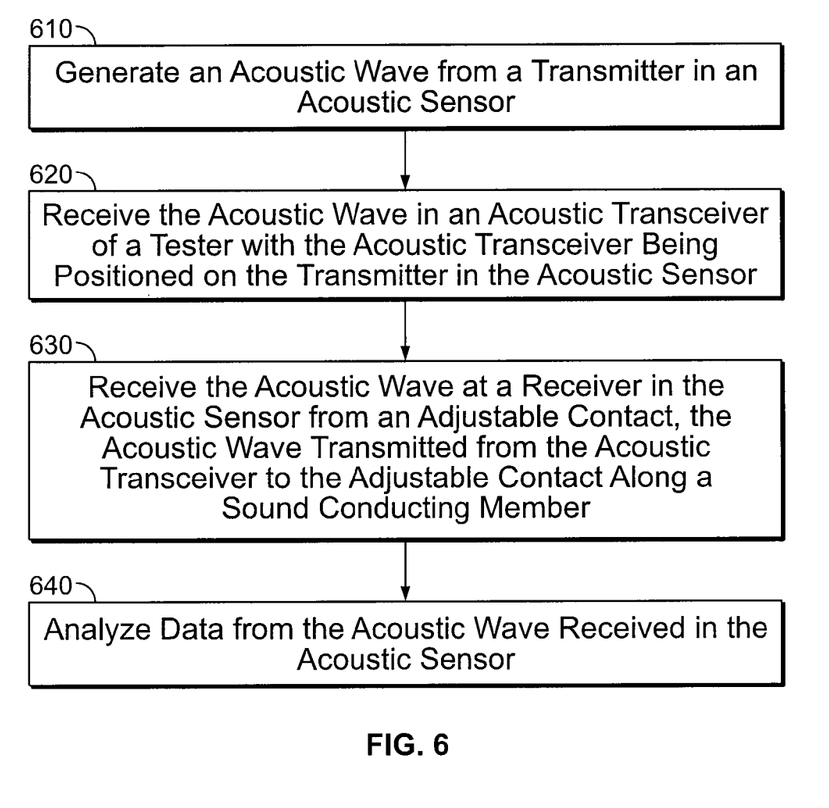
FIG. 6 shows features of an example method of testing an acoustic sensor, in accordance with various embodiments.

FIG. 6 shows features of an embodiment of an example method of testing an acoustic sensor. The acoustic sensor can be tested using a tester that includes a sound conducting member having a first end region, a second end region, and a sound conducting portion between the first and second end regions, where the first region is coupled to an acoustic transceiver of the tester. The tester can include an adjustable contact coupled to the second end region, were the adjustable contact is arranged to selectively contact a receiver in the acoustic sensor when the acoustic transceiver is positioned on the transmitter of the acoustic sensor. At 610, an acoustic wave is generated from a transmitter in an acoustic sensor. Generating the acoustic wave from the transmitter can include generating the acoustic wave at a specified frequency. At 620, the acoustic wave is received in an acoustic transceiver of a tester with the acoustic transceiver being positioned on the transmitter in the acoustic sensor.

At 630, the acoustic wave is received at a receiver in the acoustic sensor from an adjustable contact, where the acoustic wave is transmitted from the acoustic transceiver to the adjustable contact along a sound conducting member. Receiving the acoustic wave at the receiver can include automatically transmitting the acoustic wave, which is transmitted from the acoustic transceiver to the adjustable contact along the sound conducting member in response to the acoustic transceiver receiving the acoustic wave, based on a mechanical structure of the acoustic transceiver. The mechanical structure of the acoustic transceiver can include a stethoscope head. The acoustic wave received in the receiver from the adjustable contact can be recorded in a memory of the acoustic sensor. The acoustic wave can be received at a plurality of receivers of the acoustic sensor.

At 640, data from the acoustic wave received in the acoustic sensor is analyzed. Analyzing data can include using information correlated to the specified frequency at which the acoustic wave is generated from the transmitter. A plurality of acoustic waves can be generated, where each one of the acoustic waves is associated with a different one of a plurality of receivers of the acoustic sensor. This can be accomplished by adjusting the adjustable contacts such that a desired receiver is selected when one of the acoustic waves is generated. The plurality of acoustic waves can be used to analyze the status of the plurality of receivers. The features shown in FIG. 6 may be used with components and procedures associated with FIGS. 1-5 and FIGS. 7 and 8.

Figure 7:
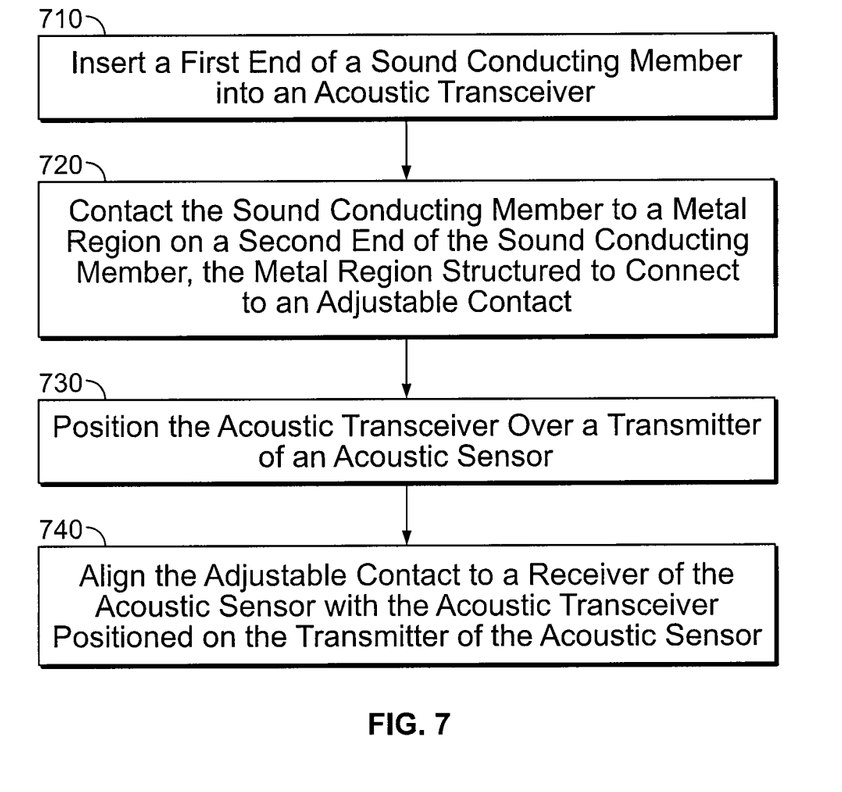
FIG. 7 shows features of an example method of operating a tester, in accordance with various embodiments.

FIG. 7 shows features of an embodiment of an example method of operating a tester. At 710, a first end of a sound conducting member is inserted into an acoustic transceiver. Inserting the first end of a sound conducting member into the acoustic transceiver can include inserting the first end of a sound conducting member into a stethoscope head. At 720, the sound conducting member is contacted to a metal region on a second end of the sound conducting member, where the metal region is structured to connect with an adjustable contact. At 730, the acoustic transceiver is positioned over a transmitter of an acoustic sensor. At 740, the adjustable contact can be aligned to a receiver of the acoustic sensor with the acoustic transceiver positioned on the transmitter of the acoustic sensor. Aligning the adjustable contact to the receiver can include using a swivel portion at an end of the adjustable contact. Additional adjustable contacts can be aligned to an array of receivers of the acoustic sensor with the acoustic transceiver positioned on the transmitter of the acoustic sensor.

Further, a suction cup can be placed on the receiver of the acoustic sensor, where the suction cup is arranged with the adjustable contact extending through the suction cup from the sound conducting member. In addition, hook and loop straps can be used to couple to the acoustic sensor such that the acoustic transceiver, the sound conducting member, and the adjustable contact are positioned to test the acoustic sensor. Once positioned, the acoustic transceiver, the sound conducting member, and the adjustable contact can be used in testing the acoustic sensor. The features shown in FIG. 7 may be used with components and procedures associated with FIGS. 1-6 and FIG. 8.

Figure 8:
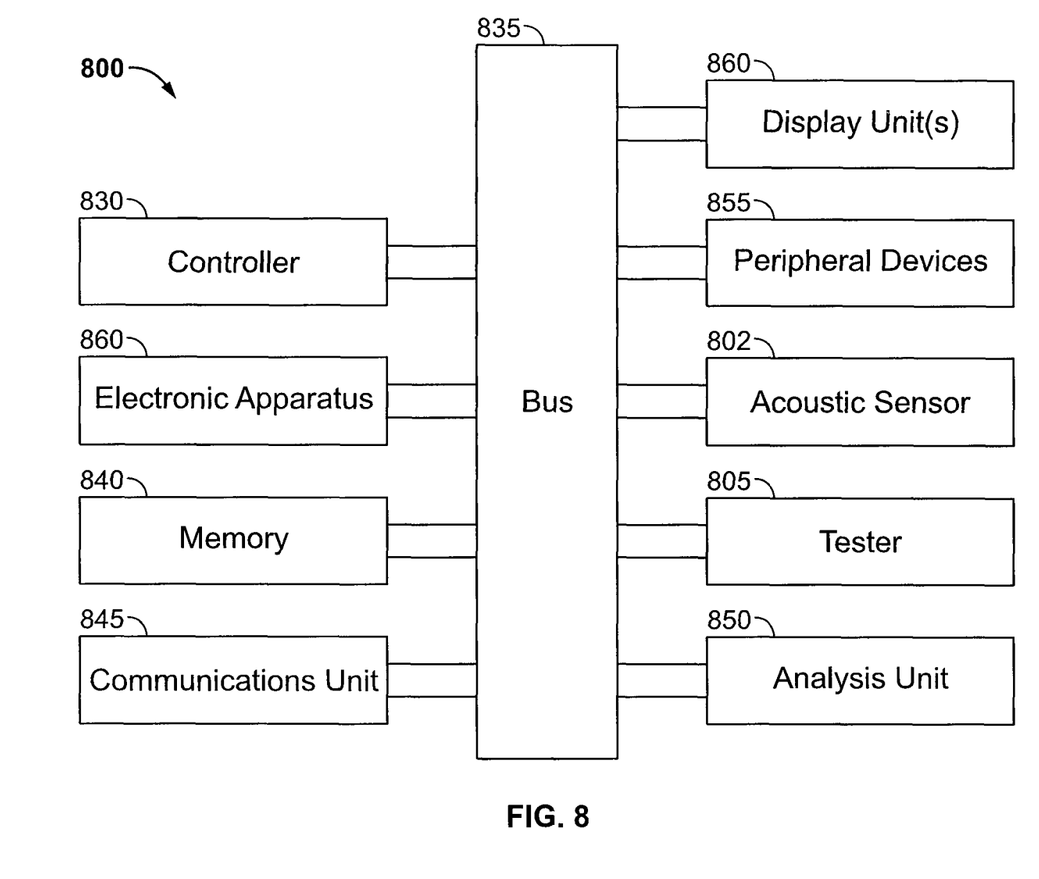
FIG. 8 depicts a block diagram of features of an example system that can be used with a tester in testing an acoustic sensor, in accordance with various embodiments.

FIG. 8 depicts a block diagram of features of an example embodiment of a system 800 having components that can assist in the implementation of a tester 805 to test an acoustic sensor 802. System 800 includes tester 805 having an acoustic transceiver, an adjustable contact, and a sound conducting member coupling the acoustic transceiver to the adjustable such that, in testing acoustic sensor 802, the adjustable contact is arranged to selectively contact a receiver of the acoustic sensor when the acoustic transceiver is positioned on a transmitter of the acoustic sensor 802. Tester 805 can be realized and operated in a similar or identical manner to arrangements discussed herein.

System 800 can include a controller 830, a memory 840, an electronic apparatus 860, and a communications unit 845. Controller 830, memory 840, and communications unit 845 can be arranged to operate as a processing unit to control activation of acoustic sensor 802, collection of signals in acoustic sensor 802, and to perform one or more operations on the signals collected by acoustic sensor 802 to determine the status of the components of acoustic sensor 802. An analysis unit to engage in analysis of data in a measurement of acoustic sensor 802 can be distributed among the components of system 800 including electronic apparatus 860. Alternatively, system 800 can include an analysis unit 850 to control activities of acoustic sensor 802 and to manage processing schemes in accordance with measurement procedures and signal processing as described herein.

Communications unit 845 can be configured to collect data from acoustic sensor 802 and distribute the data to components of system 800. Communications unit 845 may use combinations of wired communication technologies and wireless technologies to distribute data among the components of system 800.

System 800 can also include a bus 835, where bus 835 provides electrical conductivity among the components of system 800. Bus 835 can include an address bus, a data bus, and a control bus, each independently configured. Bus 835 can be realized using a number of different communication mediums that allows for the distribution of components of system 800. Use of bus 835 can be regulated by controller 830.

In various embodiments, peripheral devices 855 can include displays, additional storage memory, and/or other control devices that may operate in conjunction with controller 830 and/or memory 840. In an embodiment, controller 830 is realized as a processor or a group of processors that may operate independently depending on an assigned function. Peripheral devices 855 can be arranged with a display that can be used with instructions stored in memory 840 to implement a user interface to manage the operation of acoustic sensor 802 and/or components distributed within system 800. Such a user interface can be operated in conjunction with communications unit 845 and bus 835.

A machine-readable device can include machine-executable instructions, such as a computer-readable storage device having computer-executable instructions, for operating the system to control activation of an acoustic sensor with a tester attached to the acoustic sensor, to collect in the acoustic sensor the acoustic wave activated by the acoustic sensor and propagated along the tester, and to analyze data from the collected acoustic wave. A machine-readable device can be realized as an electronic memory device, a magnetic memory device, an optical memory device, or combinations thereof.

Apparatus to test an acoustic sensor and methods associated with the apparatus, as taught herein, provide an isolated mechanical coupling between the transmitter of an acoustic sensor and the receiver array of the acoustic sensor. Such apparatus and methods also provide a mechanism for consistent repeatable measurements. These testers can be structured in a form that is compact and easily portable and can be used at a rig site. The tester providing a transmission path from transmitter to receiver of an acoustic sensor does not require use of batteries. These testers can provide a true acoustic measurement between the transmitter and the receivers of an acoustic sensor.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. An apparatus to test an acoustic sensor comprising:
   an acoustic transceiver;
   a sound conducting member having a first end region, a second end region, and a sound conducting portion between the first and second end regions, the first end region coupled to the acoustic transceiver; and
   an adjustable contact coupled to the second end region, the adjustable contact arranged to selectively contact a receiver of an acoustic sensor when the acoustic transceiver is positioned on a transmitter of the acoustic sensor.

2. The apparatus of claim 1, wherein the acoustic transceiver includes a stethoscope head.

3. The apparatus of claim 1, wherein the sound conducting portion includes a flat piece of metal or a metal rod.

4. The apparatus of claim 3, wherein the flat piece of metal includes steel.

5. The apparatus of claim 3, wherein the metal rod includes steel.

6. The apparatus of claim 1, wherein the adjustable contact is positioned through a metal region on the second end and through an insulating material, the insulating material arranged to contact the acoustic sensor such that the insulating material separates the metal region from the acoustic sensor when the apparatus is coupled to the acoustic sensor.

7. The apparatus of claim 6, wherein the adjustable contact is arranged as a screw in a nut such that adjustment of the screw is based on movement via the nut, the nut affixed to the metal region.

8. The apparatus of claim 7, wherein the nut affixed to the metal region includes the nut welded to the metal region.

9. The apparatus of claim 1, wherein the adjustable contact includes a swivel portion at an end of the adjustable contact to contact the receiver of the acoustic sensor, the swivel portion operable to provide correction to an alignment error when coupling to the acoustic sensor.

10. The apparatus of claim 1, wherein the apparatus includes hook and loop straps to operatively couple the apparatus to the acoustic sensor.

11. The apparatus of claim 1, wherein the apparatus includes a material covering the sound conducting portion, the material select to substantially isolate an acoustic wave within the sound conducting portion.

12. The apparatus of claim 11, wherein the apparatus includes a rubber hose.

13. The apparatus of claim 1, wherein the apparatus includes a suction cup through which the adjustable contact extends from the sound conducting member, the suction cup provided to operatively channel an acoustic wave to the receiver and to align the adjustable contact to the receiver.

14. The apparatus of claim 1, wherein the apparatus includes one or more additional adjustable contacts coupled to the second end region.

15. The apparatus of claim 14, wherein the one or more additional adjustable contacts are arranged to selectively contact an array of receivers of the acoustic sensor.

16. A method comprising:
   generating an acoustic wave from a transmitter in an acoustic sensor;
   receiving the acoustic wave in an acoustic transceiver of a tester with the acoustic transceiver being positioned on the transmitter in the acoustic sensor, the tester including:
      a sound conducting member having a first end region, a second end region, and a sound conducting portion between the first and second end regions, the first region coupled to the acoustic transceiver; and
      an adjustable contact coupled to the second end region, the adjustable contact arranged to selectively contact a receiver in the acoustic sensor when the acoustic transceiver is positioned on the transmitter of the acoustic sensor;
   receiving the acoustic wave at the receiver in the acoustic sensor from the adjustable contact, the acoustic wave transmitted from the acoustic transceiver to the adjustable contact along the sound conducting member; and
   analyzing data from the acoustic wave received in the acoustic sensor.

17. The method of claim 16, wherein receiving the acoustic wave at the receiver includes automatically transmitting the acoustic wave, the acoustic wave transmitted from the acoustic transceiver to the adjustable contact along the sound conducting member in response to the acoustic transceiver receiving the acoustic wave, based on a mechanical structure of the acoustic transceiver.

18. The method of claim 17, wherein the mechanical structure of the acoustic transceiver includes a stethoscope head.

19. The method of claim 16, wherein the method includes recording the acoustic wave in a memory of the acoustic sensor.

20. The method of claim 16, wherein generating the acoustic wave from the transmitter includes generating the acoustic wave at a specified frequency and analyzing data includes using information correlated to the specified frequency.

21. The method of claim 16, wherein the method includes receiving the acoustic wave at a plurality of receivers of the acoustic sensor.

22. The method of claim 16, wherein the method includes generating a plurality of acoustic waves, each one of the acoustic waves associated with a different one of a plurality of receivers of the acoustic sensor; and analyzing the status of the plurality of receivers.

23. A non-transitory machine-readable storage device having instructions stored thereon, which, when performed by a machine, cause the machine to perform operations, the operations comprising operations to:
   generate an acoustic wave from a transmitter in an acoustic sensor;
   receive the acoustic wave in an acoustic transceiver of a tester with the acoustic transceiver being positioned on the transmitter in the acoustic sensor, the tester including:
      a sound conducting member having a first end region, a second end region, and a sound conducting portion between the first and second end regions, the first region coupled to the acoustic transceiver; and an adjustable contact coupled to the second end region, the adjustable contact arranged to selectively contact a receiver in the acoustic sensor when the acoustic transceiver is positioned on the transmitter of the acoustic sensor;

receive the acoustic wave at the receiver in the acoustic sensor from the adjustable contact, the acoustic wave transmitted from the acoustic transceiver to the adjustable contact along the sound conducting member; and analyze data from the acoustic wave received in the acoustic sensor.

24. A method comprising:

inserting a first end of a sound conducting member into an acoustic transceiver;

contacting the sound conducting member to a metal region on the second end of the sound conducting member, the metal region structured to connect with an adjustable contact;

positioning the acoustic transceiver over a transmitter of an acoustic sensor; and aligning the adjustable contact to a receiver of the acoustic sensor with the acoustic transceiver positioned on the transmitter of the acoustic sensor.

25. The method of claim 24, wherein inserting the first end of the sound conducting member into the acoustic transceiver includes inserting the first end of the sound conducting member into a stethoscope head.

26. The method of claim 24, wherein aligning the adjustable contact to the receiver includes using a swivel portion at an end of the adjustable contact.

27. The method of claim 24, wherein the method includes aligning additional adjustable contacts to an array of receivers of the acoustic sensor with the acoustic transceiver positioned on the transmitter of the acoustic sensor.

28. The method of claim 24, wherein the method includes:

placing a suction cup on the receiver, the suction cup arranged with the adjustable contact extending through the suction cup from the sound conducting member; and using hook and loop straps to couple to the acoustic sensor such that the acoustic transceiver, the sound conducting member, and the adjustable contact are positioned to test the acoustic sensor.

29. The method of claim 24, wherein the method includes testing the acoustic sensor using the acoustic transceiver, the sound conducting member, and the adjustable contact.

30. The non-transitory machine-readable storage device of claim 23, wherein the operation to generate the acoustic wave from the transmitter includes generating the acoustic wave at a specified frequency and analyzing data includes using information correlated to the specified frequency.

31. The non-transitory machine-readable storage device of claim 23, wherein the operations include an operation to generate a plurality of acoustic waves, each one of the acoustic waves associated with a different one of a plurality of receivers of the acoustic sensor; and analyzing the status of the plurality of receivers.

* * * * *